United States Patent [19]
Dostalek

[11] Patent Number: 5,277,231
[45] Date of Patent: Jan. 11, 1994

[54] STYLET FORMER

[75] Inventor: John D. Dostalek, Shoreview, Minn.

[73] Assignee: Medtronic, Inc., Minneapolis, Minn.

[21] Appl. No.: 871,464

[22] Filed: Apr. 21, 1992

[51] Int. Cl.$^5$ ............................................... B21F 1/00
[52] U.S. Cl. ..................................... 140/106; 140/123
[58] Field of Search ..................... 140/102.5, 106, 123

[56] References Cited

U.S. PATENT DOCUMENTS

| | | | |
|---|---|---|---|
| 762,691 | 6/1904 | Corrigan | 140/106 |
| 1,666,801 | 4/1928 | Varney | 140/106 |
| 3,199,549 | 8/1965 | Wallshein | 140/106 |
| 3,229,727 | 1/1966 | Kenlon | 140/102.5 |

Primary Examiner—Lowell A. Larson
Attorney, Agent, or Firm—Michael J. Jaro; Harold R. Patton

[57] ABSTRACT

A method and apparatus for imparting a reproducible curve formation to a wire stylet. The stylet former comprises a substantially cylindrical forming body having a conically tapered end. A semi-rigid forming arm is coupled to an axle extending axially outward from the tapered end of the forming body. The tapered end has a plurality of circumferential grooves of different radii disposed therein, for receiving a stylet to be formed. The forming arm is depressed over a stylet engaged in one of the forming grooves, compressing the stylet against a portion of the circumference of the forming body. At the same time, the stylet is withdrawn while pressure is maintained to keep the stylet in the forming groove. The angle with which the stylet is withdrawn from the stylet former can be varied to produce various right- and left-hand spiral curves in the stylet. The radius of curvature of the resulting stylet formation is determined by the radius of the groove in which the stylet is engaged. The length of the stylet to be formed is determined by placement of the stylet in the stylet former. A codification of the various parameters associated with the stylet formation procedures allows a given stylet formation to be uniquely described with a simple alphanumeric code. Using the parameters defined in the code will allow a given stylet formation to be recorded and consistently reproduced when desired.

8 Claims, 8 Drawing Sheets (top view)

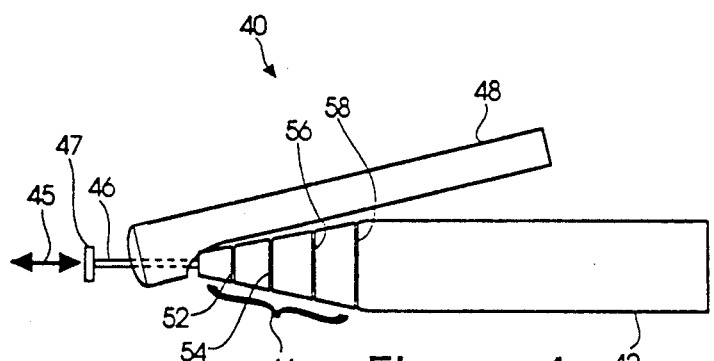
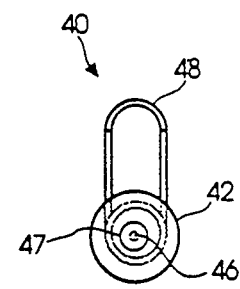
Figure 4a (top view)
Figure 4b (end view)
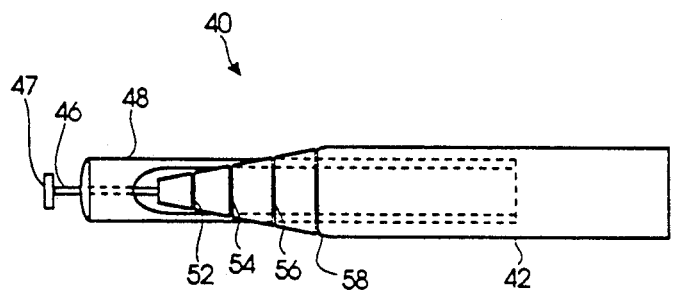
Figure 4c (side view)

STYLET FORMER

FIELD OF THE INVENTION

This invention relates to the medical arts, and more particularly to the implantation of leads, such as pacemaker pacing and sensing leads, in a human.

BACKGROUND OF THE INVENTION

In the medical field, various types of implantable leads are known and used. Particularly in the field of pacemakers, the use of implanted, transvenous pacing and/or sensing leads is very common. Pacemakers are typically implanted either in or outside the thoracic cavity, for example, under the skin near the patient's right clavicle, or in the patient's abdomen. An endocardial pacemaker lead, having a proximal end electrically coupled to the pacemaker and a distal end disposed within a chamber of the heart, conducts stimulating pulses from the pacemaker's pulse generator to the patient's heart, and/or conducts electrical cardiac signals from the patient's heart to the pacemaker's sensing circuitry.

One advantage of modern pacemaker systems is that the implant procedures are relatively simple and atraumatic, involving only a minimal amount of invasive surgery. The implant procedure can be performed under local anesthesia. Typically, an endocardial lead is introduced into the patient through a small incision at or near the implant site, usually just below and slightly medial to the junction of the middle and inner third of the clavicle. The distal end of the lead is first introduced into the patient's subclavian vein using any one of various introducer techniques known in the art. Then, the implanting physician directs the distal end of the lead through the vein and into the heart, by manipulating the proximal end of the lead. Once the lead is positioned, the proximal end is connected to the pacemaker. A somewhat larger incision is then made at the implant site, allowing the pacemaker to be inserted under the skin.

Pacemaker leads typically comprise a one or more coiled conductors surrounded by a resilient, bio-compatible insulative coating of silicon rubber or polyurethane. One or more pacing or sensing electrodes are disposed at or near the distal end of the lead body, and a connector pin for connection to the connector block of a pacemaker is disposed at the proximal end of the lead body. The insulated conductor is coiled to enhance the flexibility of the lead body and to reduce the possibility of metal fatigue and consequent lead failure due to flexing of the lead. The flexibility of the lead, while desirable from the standpoint of patient safety and comfort, makes the process of inserting the lead into the patient's heart somewhat difficult.

In order to facilitate the introduction of a lead into the patient's heart, a so-called "stylet" can be employed. As would be known to one of ordinary skill in the pacemaker art, a stylet is a relatively stiff wire that may be used during the lead implantation procedure to give the lead increased rigidity. In order to use a stylet, the connector pin of the pacemaker lead must be designed to permit insertion of the stylet into the cylindrical bore, or lumen, defined by the coiled lead conductor. The stylet can thus be inserted axially into the lead from the connector end and pushed into the lead so that the stylet runs along its entire length, increasing the lead's rigidity during the introduction procedure. A knurled end-piece disposed on the proximal end of the stylet allows the physician to manipulate the lead and navigate the distal end of the lead through the patient's venous system to the heart, by pushing and twisting the stylet. Once the lead is positioned, and before the lead is coupled to the pacemaker, the stylet is withdrawn from the lead, thus restoring the lead's flexibility.

Often, the physician will impart a curve to the stylet, so that after insertion of the stylet into the lead, the curve is imparted to the lead itself. The curvature of the stylet, and hence the lead, can facilitate the navigation of the lead through the venous system. For example, a curve near the distal end of the stylet (and thus, near the distal end of the lead as it is being introduced), can help the physician direct the lead around curves or corners in the subclavian vein. Once in the heart, the curved stylet can help to direct the distal tip of the lead to various structures within the heart, e.g., to the coronary sinus, to the atrial appendage, or across the tricuspid valve to the right ventricle.

In the prior art, the techniques used for imparting a curve to a stylet have been relatively primitive. For example, the physician may draw the stylet around the cylindrical body of a syringe, or around the edge of some surgical instrument, while keeping the stylet in contact with the syringe body or surgical instrument by pressing on the stylet with a thumb or finger. Such impromptu techniques, although commonly practiced, are deemed by the inventor to be undesirable for several reasons. First, it is important for the entire surface, and especially the distal tip of the stylet, to be smooth and free from kinks, sharp edges, or burrs that could damage the coiled lead conductor as the stylet is being inserted into or withdrawn from the lead. If an object that is too hard or that has sharp edges is used in the formation of a curve in a stylet, the stylet may be abraded or otherwise damaged. Abrasions on the stylet may make insertion of the stylet into the lumen of the lead difficult or impossible. Also, it is difficult to maintain constant contact between the stylet and the forming object with only a thumb or finger; this is particularly true at the extreme distal end of the stylet. If the stylet is not kept in contact with the forming body all the way to its distal end, the distal end may be irregularly curved.

A second perceived deficiency such improvisational prior art techniques for stylet forming may be difficult to repeat with consistent results; thus, a physician who discovers a particularly suitable and effective stylet formation may not be able to consistently reproduce such a formation.

It is believed by the inventor, therefore, that it would be desirable to provide physicians with an improved means for imparting a curve to a stylet. In particular, it is believed that there is a need for a stylet forming technique which does not damage the stylet, and which is repeatable with consistent results.

SUMMARY OF THE INVENTION

In accordance with the present invention, a method and apparatus for safely and consistently imparting a curve to a stylet is provided. In one embodiment of the invention, a cylindrical forming body with one or more circumferential grooves therein is provided with a semi-rigid arm. The stylet is placed in one of the grooves, and held in place between the forming body and the forming arm. The stylet is pressed against a portion of the former's circumference as the stylet is pulled out from between the arm and the former, thereby imparting a smooth curve to the stylet.

The stylet former in accordance with one disclosed embodiment of the invention has the advantages of being safe and simple to use, even with a gloved hand, and also inexpensive (and thus may be considered disposable). In addition, a codification of various parameters associated with the use of the disclosed stylet former, such as the radius of the forming body, the pull angle, length of formation, and so on, allows a given stylet formation to be identified by a simple alphanumeric code. With such a codification, a particular stylet formation can be recorded and reproduced whenever necessary.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein:

FIGS. 4a, 4b, and 4c are top, end, and side views, respectively, of a stylet former in accordance with one embodiment of the present invention;

DETAILED DESCRIPTION OF A SPECIFIC EMBODIMENT OF THE INVENTION

Figure 1:
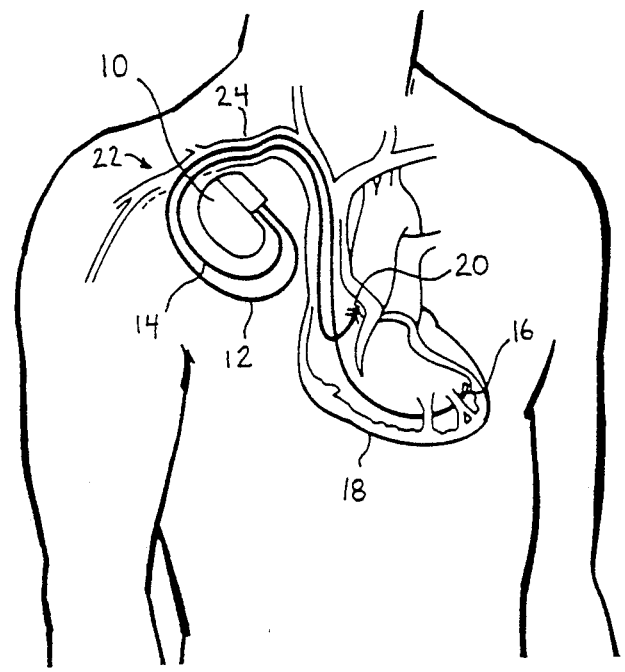
FIG. 1 is an illustration of a pacemaker system implanted in a patient.

Referring to FIG. 1, a typical pacemaker system as it is implanted in a human patient is shown. The pacemaker system of FIG. 1 includes a pacemaker 10 and two leads 12 and 14. Lead 12 is a ventricular lead, having its distal end 16 disposed in the right ventricle of the patient's heart 18. Lead 14 is an atrial lead having its distal end 20 disposed in the right atrium of heart 18. Leads 12 and 14 are introduced into the patient by way of an incision generally in the region designated as 22 in FIG. 1, and run through subclavian vein 24 into heart 18.

Figure 2:
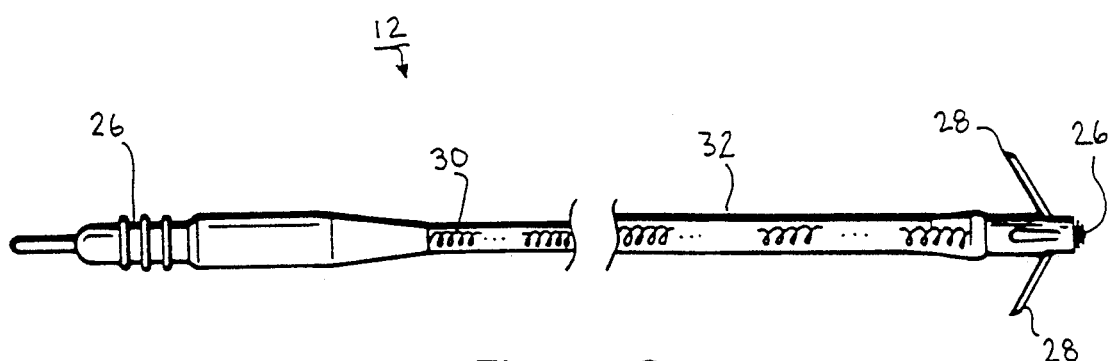
FIG. 2 is an illustration of a pacing lead from the pacemaker system of FIG. 1.

In FIG. 2, an enlarged view of pacemaker lead 12 is shown. At the proximal end of lead 12, a connector pin 26 is disposed. At the distal end of lead 12, an electrode 26 is exposed, so that lead 12 can conduct electrical signals between heart 18 and pacemaker 10. Electrode 12 is provided with tines 28 which facilitate stable placement in heart 18. The body of lead 12 comprises a coiled conductor 30 surrounded by a flexible, insulating layer 32 of silicone rubber, polyurethane, or other suitable bio-compatible material. Coiled conductor 30 defines a cylindrical lumen through the length of lead 12; connector pin 26 is designed to allow insertion of a stylet into the lumen of lead 12.

Figure 3:
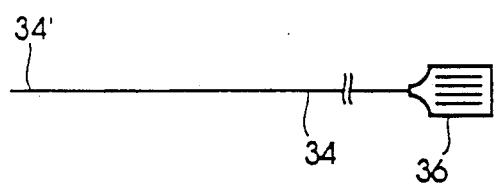
FIG. 3 is an illustration of a stylet.

Turning now to FIG. 3, a stylet 34 is shown. Stylet 34 is preferably a stainless steel wire, and has a knurled handle 36 on its proximal end. As previously noted, it is important for stylet 34 to be smooth and free from burrs and abrasions at its distal end or anywhere along its length, so that coiled conductor 30 in lead 12 is not damaged as the stylet passes through, and stylet 34 easily passes into and through the lumen of lead conductor 30.

FIGS. 4a, 4b, and 4c, are top, end, and side views, respectively, of a stylet former 40 in accordance with one embodiment of the present invention. As can be seen from FIG. 4a, stylet former 40 comprises a substantially cylindrical forming body 42 having a tapered end 44. An axle 46 extends axially out from tapered end 44 of forming body 42. Stylet former 40 further comprises a forming arm 48, with axle 46 extending at an angle through one end thereof. A retaining nut 47 may be provided at the distal end of axle 46 to prevent former arm 48 from being separated from former body 42. From FIGS. 4a, 4b, and 4c, it should be apparent that forming arm 48 comprises a substantially cylindrical shell with a semi-cylindrical section thereof cut away along most of its length. Thus, along most of its length, arm 48 has a substantially inverted "U" shaped cross section, while at the end through which axle 46 extends, arm 48 has a full circular cross-section. As shown in FIG. 4a, arm 48 is capable of sliding back and forth along axle 46, in the direction indicated by arrow 45, to facilitate insertion of a stylet between forming body 42 and forming arm 48, as will be hereinafter described.

With continued reference to FIGS. 4a, 4b, and 4c, and in particular to FIG. 4a, tapered end 44 of cylindrical former body 42 is provided with a plurality of circumferential grooves, four such grooves being shown and designated in FIG. 4a as 52, 54, 56, and 58. In the presently preferred embodiment, stylet former 40 has the following dimensions, approximately: former body 42 is approximately 6-cm long overall, with approximately 2.5-cm of former body 42 comprising tapered end 44; former body 42 is approximately 1.2-cm in diameter throughout its un-tapered portion, and tapered portion 44 has a circumference ranging from 1.2-cm down to 0.5-cm. Former arm 48 is also approximately 6-cm long overall. Axle 46 extends approximately 2.5-cm axially outward from tapered end 44 of former body 42. Grooves 52, 54, 56, and 58 are each approximately 0.02- to 0.03-cm deep, with groove 52 being approximately 0.6-cm in from the end of former body 42, (on the tapered end).

In the presently preferred embodiment of the invention, cylindrical forming body 42 is made of nylon or another suitably rigid, smooth, and sterilizable material. Axle 46 is preferably metal, and arm 48 is preferably made of a suitably resilient but not entirely rigid material such as nylon, polyurethane or the like. The ability of arm 48 to flex is necessary for the presently disclosed embodiment of the invention, as will be hereinafter described.

Figure 5A:
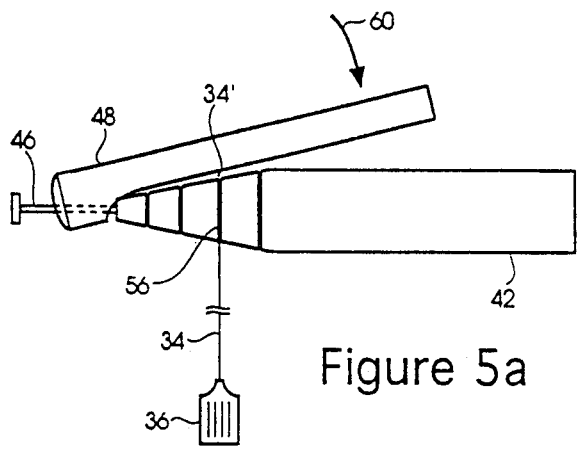
FIGS. 5a, 5b, 5c, 5d, and 5e are illustrations showing progressive stages in the stylet formation procedure using the stylet former of FIGS. 4a, 4b, and 4c.
Figure 5B:
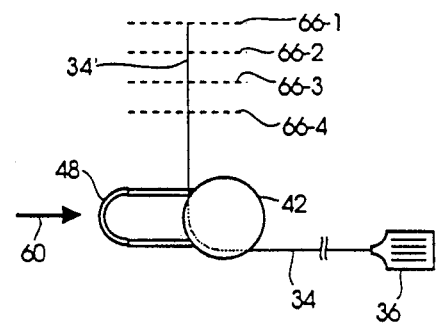

Operation of stylet former 40 will not be described with reference to FIGS. 5a, 5b, 5c, and 5d. The process of stylet forming using former 40 begins by placing the distal end 34' of stylet 34 in one of the grooves 52, 54, 56, or 58, between former body 42 and former arm 48. In FIG. 5a, stylet 34 is shown having been placed in groove 56. As shown in FIG. 5b, which is a side view of the arrangement shown in FIG. 5a, stylet 34 is placed in groove 56 between former body 42 and former arm 48 such that stylet 34 makes a smooth, right angle turn (shown in phantom in FIG. 5b) around former body 42; thus, in FIG. 5a, the distal end 34' of stylet 34 is shown as a 'dot' designated 34', indicating that distal end 34' extends as if out of the page of FIG. 5a.

Figure 5C:
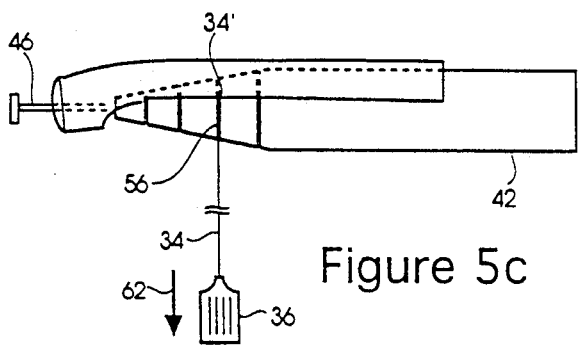
Figure 5D:
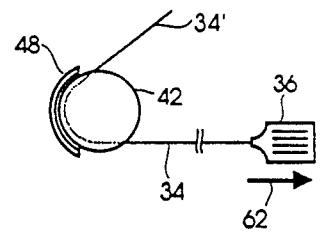
Figure 5E:
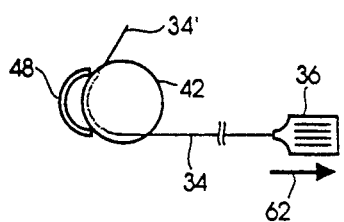

In the next stage of the forming process, the user squeezes former arm 48 down against former body 42, in the direction indicated by arrow 60 in FIGS. 5a and 5b. This squeezing can be accomplished, for example, by grasping former 40 between the thumb and forefinger of one hand. Squeezing former 40 in this way causes arm 48 to press against former body 42 as shown in FIGS. 5c and 5d. The previously noted resiliency of former arm 48 allows former arm 48 to be deformed somewhat to come into contact with former body 42. It should be noted from FIG. 5d that the inverted "U"-shape of former arm 48 is caused to widen somewhat so that it substantially conforms to the curvature of former body 42. It is the inventor's experience that different curves can be achieved depending upon whether forme arm 48 is fully pressed against former body 42 as shown in FIG. 5d, or only partially depressed as shown in FIG. 5e. For the purposes of this description, the depression of former arm 48 shown in FIG. 5d will be referred to as "full depression", and the depression of former arm 48 shown in FIG. 5e will be referred to as "half depression".

To impart a curve to stylet 34, the user next withdraws stylet 34, by pulling on endpiece 36 in the direction of arrow 62 in FIGS. 5c and 5d, while continuing to maintain the squeezing pressure to hold arm 48 against former body 42. To prevent kinking, withdrawal of stylet 34 should preferably begin slightly before or at the same time that former arm 48 is depressed.

When stylet 34 is completely withdrawn, or when the desired length of stylet to be formed has passed under former arm 48, the forming process is complete. The user can then release the squeezing pressure between arm 48 and body 42; the resiliency of arm 48 will allow arm 48 to return to its original position, as shown in FIGS. 4a, 4b, and 4c.

Figure 6:
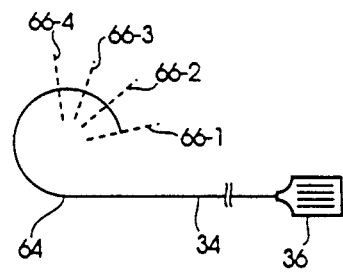
FIG. 6 is an illustration of a stylet after being formed in accordance with the formation procedure depicted in FIGS. 5a, 5b, 5c, 5d, and 5e.

A stylet formed as described with reference to FIGS. 5a through 5d above is shown in FIG. 6. Several features of the stylet formation achieved in accordance with the present invention are to be noted. First, it should be noted from FIG. 6 that no kinks or sharp bends are imparted to stylet 34 during the forming process. Significantly, there is no kink at the point designated 64 in FIG. 6, at which point the curvature begins. This is often not the case with the improvised prior art stylet forming techniques. It is also to be noted that the curvature of stylet 34 is of a constant radius from point 64 all the way to the extreme distal end 34' of stylet 34. This, too, is often not achieved with prior art stylet forming techniques, in which it is difficult to keep stylet 34, and in particular, the extreme distal end 34' of stylet 34, in constant contact with whatever forming body is used.

The amount of stylet 34 to which a curve is imparted using former 40 in accordance with the present invention will depend upon the placement of stylet 34 in former 40 at the beginning of the forming procedure. In particular, referring to FIG. 5b, the length of stylet 34 extending up from between forming body 42 and forming arm 48 can be varied. Several different lengths are designated by dashed lines 66-1, 66-2, 66-3 and 66-4 in FIG. 5b. The resulting curvature corresponding to these different lengths is indicated by dashed lines 66-1, 66-2, 66-3, and 66-4 in FIG. 6.

Figure 7A:
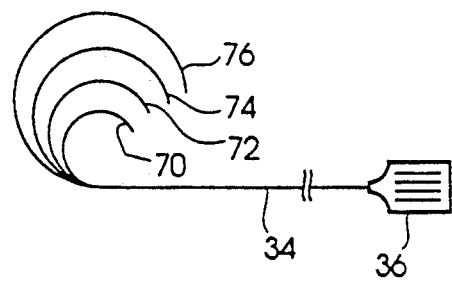
FIGS. 7a and 7b are illustrations showing different curvatures which may be imparted to a stylet using the former of FIGS. 4a, 4b, and 4c.

In accordance with an important aspect of the present invention, the radius of curvature imparted to stylet 34 by former 40 is determined by the radius of the groove 52, 54, 56, or 58 through which stylet 34 is drawn. This is illustrated in FIG. 7a, in which curve 70 is that which would result from drawing stylet 34 through groove 52 on former body 42, curve 72 corresponds to groove 54, curve 74 corresponds to groove 56, and curve 76 corresponds to groove 58. From FIG. 7a, it is apparent that radius of stylet curvature is proportional to the radius of the groove used to impart the curve to the stylet. It should be noted that since the same radius of curvature will result each time the same groove is chosen, former 40 in accordance with the presently disclosed embodiment of the invention is believed to offer reproducibility of results not attainable with techniques of the prior art.

Figure 7B:
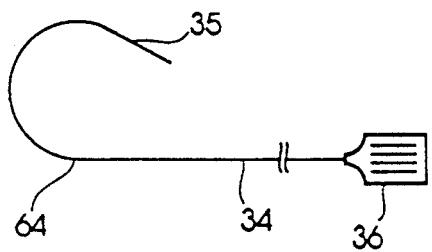

In some cases, it may be desirable to leave an unformed, straight "tail" portion at the distal end 34' of stylet 34. This can be accomplished by releasing former arm 48 before stylet 34 has been fully withdrawn from stylet former 40. As shown in FIG. 7b, this results in a straight tail segment 35 at the distal end of stylet 34.

Figure 8:
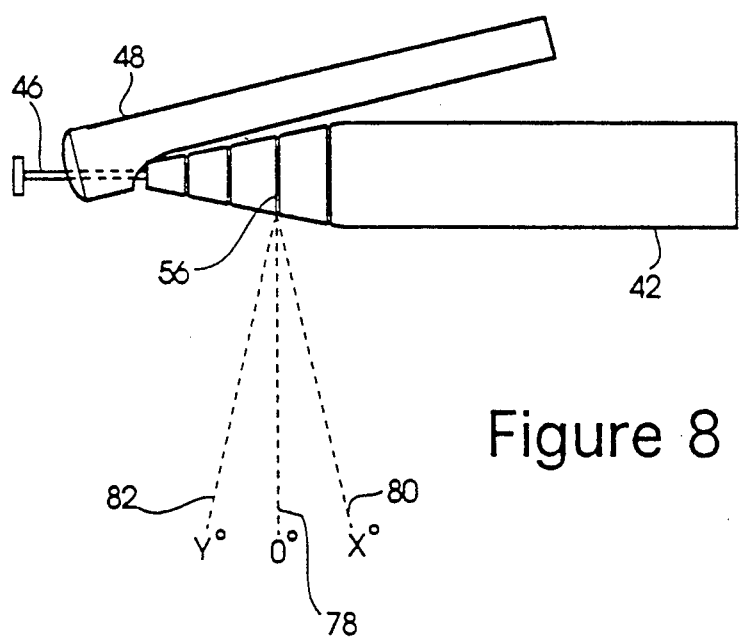
FIG. 8 is a top view of the stylet former of FIGS. 4a, 4b, and 4c, showing different pull angles relative thereto.
Figure 9A:
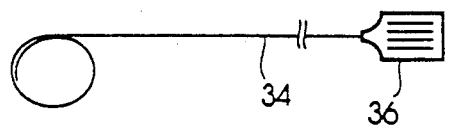
FIGS. 9a and 9b are top and side views, respectively, of a stylet formed using the stylet former of FIGS. 4a, 4b, and 4c, with a right-hand pull angle.
Figure 9C:
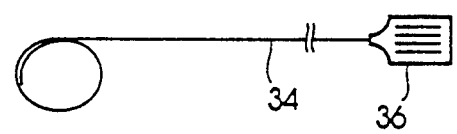
FIGS. 9c and 9d are top and side views, respectively, of a stylet formed using the stylet former of FIGS. 4a, 4b, and 4c, with a left-hand pull angle.
Figure 9B:
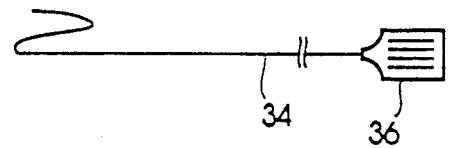
Figure 9D:
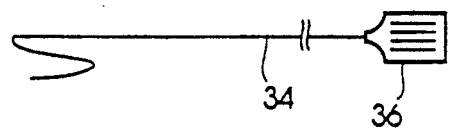

In FIGS. 5a through 5d, it was assumed that stylet 34 was drawn out of former 40 in a direction perpendicular to axle 46 of forming body 42. In accordance with another aspect of the presently disclosed embodiment of the invention, if the angle of withdrawal, or "pull angle" is changed, right- or left-hand spiral curves can be imparted to stylet 34. Referring to FIG. 8, dashed line 78 indicates the 0° pull angle of FIGS. 5a through 5d. Dashed line 80 depicts the direction of an X° positive pull angle, which results in a left-hand spiral as depicted in FIG. 9c. Dashed line 82 in FIG. 8 depicts the direction of a Y° negative pull angle, which results in a right-hand spiral curvature as depicted in FIG. 9a.

Figure 10:
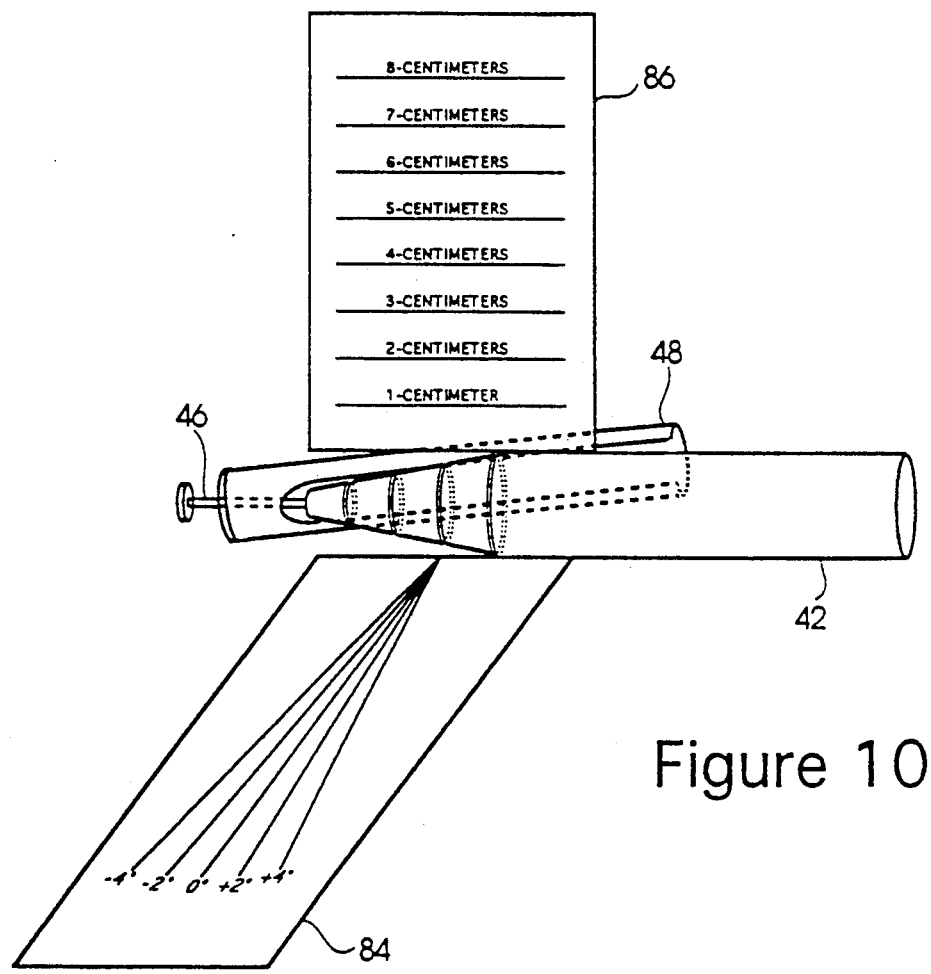
FIG. 10 is a perspective view of a the stylet former of FIGS. 4a, 4b, and 4c, with a pull angle template and a formation length template attached thereto.

Referring to FIG. 10, it is contemplated by the inventor that former 40 in accordance with the presently disclosed embodiment of the invention may be used in conjunction with a template 84 having various positive and negative pull angles printed thereon. Template 84 may be attached to former body 42 or forming arm 48 as shown in FIG. 10, as with an adhesive strip or the like. The line representing the 0° pull angle is aligned with the selected groove.

Also depicted in FIG. 10 is a second template 86 which may also be attached to former body 42 or former arm 48, and which allows the user to select the length of curvature, as discussed above with reference to FIGS. 5b and 6. Template 86 essentially serves as a frame of reference for selecting the length of stylet to be curved. Templates 84 and 86 would insure repeatability of pull angle and curve length.

It is contemplated by the inventor that any stylet curve can be uniquely described in terms of (1) groove radius; (2) length of curve; (3) pull angle; and (4) former arm depression. A codification of these factors would allow a given stylet curve to be described with a simple alphanumeric code. If grooves 52, 54, 56, and 58 were assigned numbers 1, 2, 3, and 4, respectively, then, for example, a code "3-3-0-F" would describe a curve resulting from using groove 56, with 3-cm of the distal end extending up from between former body 42 and former arm 48, a 0° pull angle, and full depression (F) of former arm 48. Similarly, a code 2-4-5-H would identify groove 2, 4-cm curve length, 5° pull angle, and half (H) depression of former arm 48.

Although a specific embodiment of the invention has been set forth herein in some detail, it is to be understood that this has been done for the purposes of illustration only, and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A forming tool adapted to impart a curve to a stylet to be placed into the lumen of a pacemaker lead, comprising:
    a substantially cylindrical forming body having a tapered end with at least one circumferential groove formed therein;
    a forming arm attached to said forming body at said tapered end and adapted to be squeezed against said tapered forming body end after a stylet has been tangentially disposed in said groove, said forming arm constituting a semi-cylindrical shell and being flexible such that said forming arm substantially conforms to said tapered end of said forming body when pressed against said tapered end;
    said forming arm holding said stylet in said groove around a portion of said tapered end's circumference to cause a curve having a radius proportional to the radius of said groove to be imparted to a portion of said stylet that is drawn against said tapered end when said stylet is tangentially withdrawn from between said forming arm and forming body.

2. A method for imparting a curve to a stylet comprising the steps of:
    disposing a stylet tangentially on a forming body;
    longitudinally positioning a resiliently deformable forming arm against said forming body and said stylet;
    pressing said forming arm against said forming body and said stylet;
    securing a portion of said stylet in between said forming body and forming arm and leaving a proximal and a distal end of said stylet extending tangentially away from said forming body; and
    imparting a curve to said distal end of said stylet by withdrawing said stylet from in between said forming body and forming arm by pulling on said proximal end of said stylet in a direction such that said distal end of said stylet is pulled against a portion of said forming body.

3. A tool adapted to impart a curve to a stylet comprising:
    a forming body having a tapered end; and
    a forming arm attached to said forming body at said tapered end and adapted to be positioned proximate to said tapered end after a stylet has been tangentially disposed proximate said tapered end, said forming arm constituting a flexible member such that said forming arm substantially conforms to said tapered end of said forming body when pressed against said tapered end, said forming arm positioning said stylet about said tapered end to cause a curve to be imparted to a portion of said stylet that is drawn against said tapered end when said stylet is axially withdrawn from between said forming arm and forming body.

4. The tool of claim 3 wherein said forming body is substantially cylindrical.

5. The tool of claim 3 wherein said tapered end of said forming body is conical and has at least one circumferential groove formed therein.

6. The tool of claim 5 wherein said forming arm substantially conforms to said conically tapered end of said forming body when pressed against said tapered end.

7. The tool of claim 3 wherein said forming arm is adapted to be squeezed against said tapered end after said stylet has been tangentially disposed in said groove.

8. The tool of claim 3 wherein said member of said forming arm comprises a semi-cylindrical shell.

* * * * *